(12) United States Patent
Kam et al.

(10) Patent No.: US 11,357,521 B2
(45) Date of Patent: Jun. 14, 2022

(54) MULTIFUNCTIONAL PCL GUIDE ARM

(71) Applicant: CONMED CORPORATION, Utica, NY (US)

(72) Inventors: Andrew Kam, Odessa, FL (US); Andrew Muser, St. Pete Beach, FL (US); Kalifa A. Clarke, Pinellas Park, FL (US); Peter Verdonk, Zwijnaarde (BE); Björn G. Barenius, Stockholm (SE); Seth L. Sherman, Columbia, MO (US); Brian R. Wolf, Iowa City, IA (US); Timothy Spalding, Leamington Spa (GB)

(73) Assignee: Conmed Corporation, Utica, NY (US)

( * ) Notice: Subject to any disclaimer, the term of this patent is extended or adjusted under 35 U.S.C. 154(b) by 213 days.

(21) Appl. No.: 16/445,257

(22) Filed: Jun. 19, 2019

(65) Prior Publication Data
US 2020/0261102 A1    Aug. 20, 2020

Related U.S. Application Data

(60) Provisional application No. 62/806,941, filed on Feb. 18, 2019.

(51) Int. Cl.
*A61B 17/17*    (2006.01)
*A61B 90/00*    (2016.01)

(52) U.S. Cl.
CPC .......... *A61B 17/1764* (2013.01); *A61B 17/17* (2013.01); *A61B 90/08* (2016.02); *A61B 90/39* (2016.02); *A61B 2090/0807* (2016.02); *A61B 2090/3966* (2016.02)

(58) Field of Classification Search
CPC .................................................. A61B 17/1764
See application file for complete search history.

(56) References Cited

U.S. PATENT DOCUMENTS

| | | | | | |
|---|---|---|---|---|---|
| 5,681,320 | A | * | 10/1997 | McGuire | A61B 17/0401 606/104 |
| 5,968,050 | A | * | 10/1999 | Torrie | A61B 17/1714 606/102 |
| 6,120,511 | A | * | 9/2000 | Chan | A61B 17/1637 606/102 |
| 6,254,606 | B1 | * | 7/2001 | Carney | A61B 17/1714 606/102 |
| 7,192,431 | B2 | * | 3/2007 | Hangody | A61B 17/1604 606/87 |

(Continued)

*Primary Examiner* — Zade Coley
(74) *Attorney, Agent, or Firm* — Bond, Schoeneck & King, PLLC; Frederick J. M. Price

(57) ABSTRACT

A drill guide arm for providing guidance for placement of a bone tunnel, while protecting against trauma. The guide arm includes a first arm at a proximal end connected at an angle to a second arm, the second arm extending to a distal end. The angle can be within the range of 80°-110°. The second arm extends along a first axis. The guide arm also includes a distal tip extending at a second angle from the second arm at the distal end, and an indicator feature extending from the distal tip toward the first arm. The indicator feature extends along a second axis, the second axis being substantially parallel to the first axis. The guide arm can also include a shield feature of the distal tip. The shield feature has a width wider than the remainder of the distal tip.

9 Claims, 5 Drawing Sheets

(56) References Cited

U.S. PATENT DOCUMENTS

| | | | |
|---|---|---|---|
| 8,801,717 B2* | 8/2014 | Herdrich | A61B 17/1764 606/86 R |
| 9,198,676 B2* | 12/2015 | Pilgeram | A61B 17/1764 |
| 9,668,750 B2 | 6/2017 | Mirochinik et al. | |
| 10,188,403 B2 | 1/2019 | Mirochinik et al. | |
| 10,531,881 B2* | 1/2020 | Sauer | A61B 17/1714 |
| 10,537,340 B2 | 1/2020 | Mirochinik et al. | |
| 2002/0143342 A1* | 10/2002 | Hangody | A61F 2/4618 606/87 |
| 2003/0051591 A1* | 3/2003 | Gobel | A61B 17/1714 83/196 |
| 2006/0271059 A1* | 11/2006 | Reay-Young | A61B 17/1764 606/96 |
| 2008/0103506 A1* | 5/2008 | Volpi | A61B 17/1714 606/96 |
| 2009/0143784 A1* | 6/2009 | Petersen | A61B 17/1714 606/96 |
| 2011/0166581 A1* | 7/2011 | Van Der Merwe | A61B 17/1764 606/96 |
| 2011/0282350 A1* | 11/2011 | Kowarsch | A61F 2/0805 606/96 |
| 2011/0313478 A1* | 12/2011 | Herdrich | A61B 17/1764 606/86 R |
| 2012/0109136 A1* | 5/2012 | Bourque | A61B 17/1714 606/87 |
| 2016/0089162 A1* | 3/2016 | Ardito | A61B 17/1714 606/98 |
| 2017/0252048 A1* | 9/2017 | Sauer | A61B 17/1764 |
| 2019/0167281 A1 | 6/2019 | Zilberman et al. | |
| 2019/0231371 A1* | 8/2019 | Maxson | A61B 34/10 |

* cited by examiner

MULTIFUNCTIONAL PCL GUIDE ARM

CROSS-REFERENCE TO RELATED APPLICATIONS

This application claims priority to U.S. Provisional Patent Application Ser. No. 62/806,941, filed on Feb. 18, 2019 and entitled "Multifunctional PCL Guide Arm," the entirety of which is incorporated herein by reference.

BACKGROUND OF THE INVENTION

1. Field of the Invention

The present invention is directed generally to surgical tools and instruments and, more particularly, to drill guide arm for providing guidance for placement of a bone tunnel.

2. Description of Related Art

During orthopedic surgeries, holes are often drilled in bones. In some procedures, a drill guide, such as that shown in FIG. 1, is used to line-up the drill to ensure the drilled tunnel is in the appropriate location. Many bone surfaces to be drilled have severe contours that vary from patient to patient. Due to the contours, it can be difficult to properly seat the drill guide against the bone. This is particularly true when the drill guide is used to assist in drilling a femoral bone tunnel during PCL reconstruction.

Many conventional drill guide assemblies are used in conjunction with a guide body, guide arm, and drill guide sleeve. Conventional drill guide assemblies also require a threaded mechanism to prevent the guide arm from falling out of the drill guide assembly. In some instances, current drill guide assemblies require additional instruments for the surgical procedure. As the number of instruments, parts, and pieces increases, the risk of potential concomitant damage to surrounding structures increases. This increased risk is due to the number of times an instrument or part is inserted and removed from the surgical site.

Therefore, there is a need for a drill guide device or system that incorporates multiple features, reducing the quantity of instruments or parts used at a surgical site.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

SUMMARY OF THE INVENTION

Embodiments of the present invention are directed to a drill guide arm that is optimal for providing guidance for placement/formation of a bone tunnel, while protecting against trauma. According to one aspect, the guide arm includes a first arm at a proximal end connected at a first angle to a second arm. The second arm extends to a distal end along a first axis. The first angle can be within the range of 80°-110°. The guide arm also includes a distal tip extending at a second angle from the second arm at the distal end and an indicator feature extending from the distal tip toward the first arm. The indicator feature extends along a second axis and the second axis is substantially parallel to the first axis.

According to another aspect, the guide arm includes a first arm at a proximal end connected at an angle to a second arm. The second arm extends to a distal end along a first axis. The angle can be within range of 80°-110°. The guide arm also includes a distal tip extending from the second arm at the distal end and a shield feature of the distal tip. The shield feature has a width wider than the remainder of the distal tip. In an embodiment, the shield feature includes an aperture extending therethrough which is configured to receive a guide pin.

These and other aspects of the invention will be apparent from and elucidated with reference to the embodiment(s) described hereinafter.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
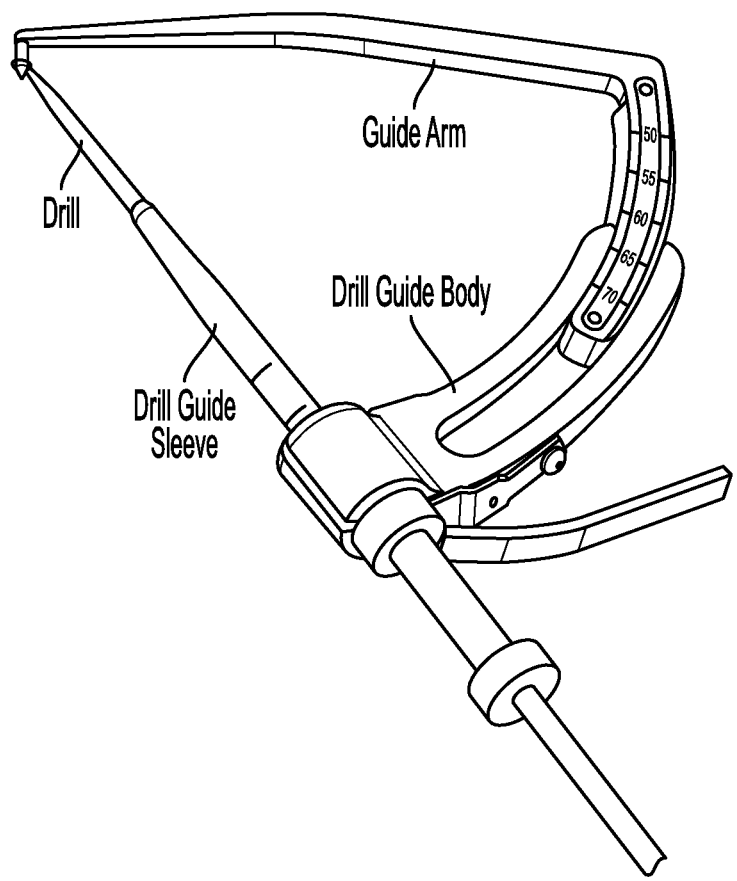
FIG. 1 is a perspective view schematic representation of a drill guide assembly of the prior art.
Figure 2:
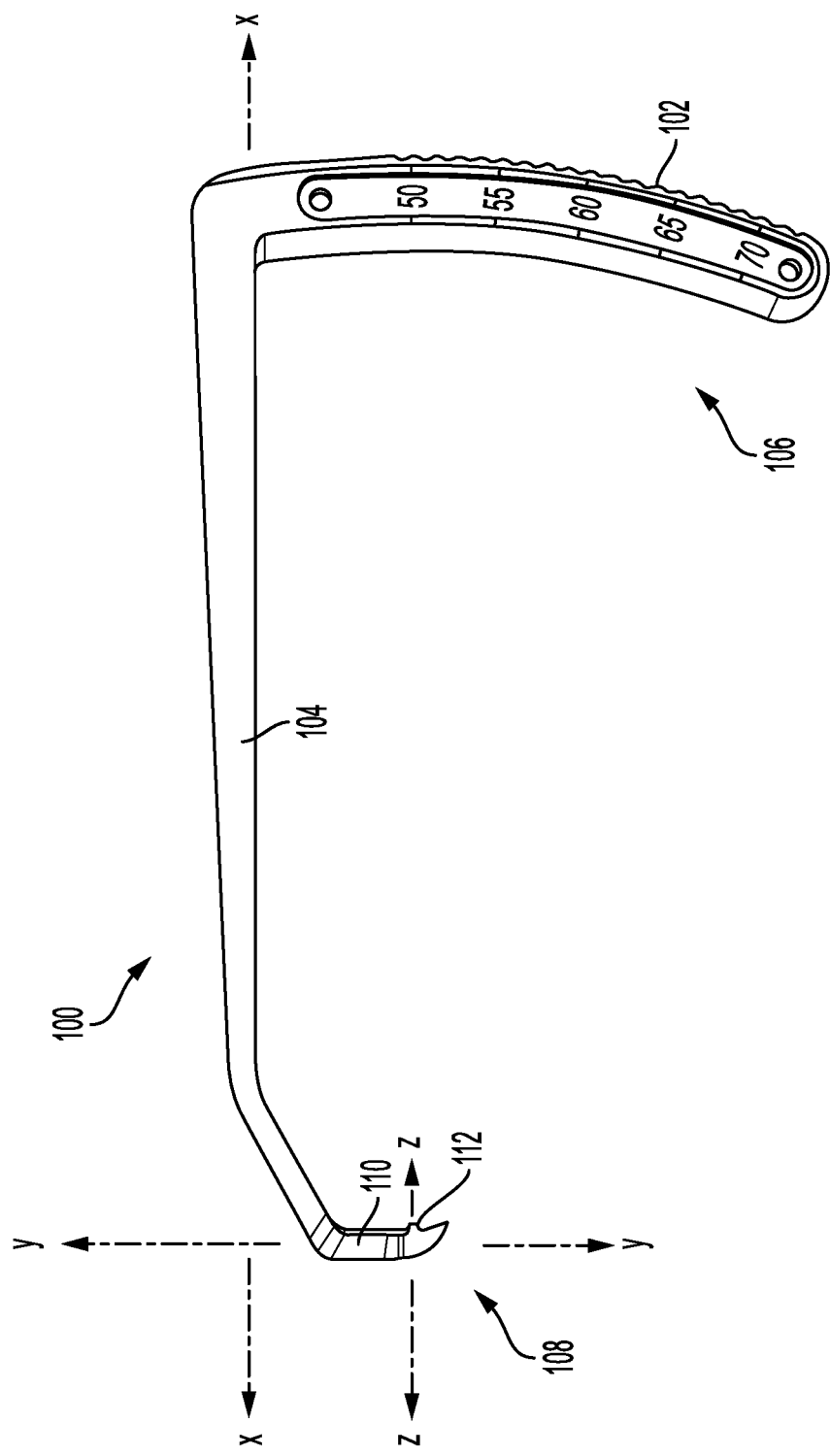
FIG. 2 is a side view schematic representation of a drill guide arm, according to an embodiment.

Referring now to the figures, wherein like reference numerals refer to like parts throughout, FIG. 2 shows a side view schematic representation of a drill guide arm 100, according to an embodiment. The drill guide arm 100 is generally L-shaped, comprising a first arm 102 (or stem) connected at an angle (e.g., 80°-110°) to a second arm 104. In a preferred embodiment, the first arm 102 is connected to the second arm 104 at angle within the range of 90°-100°. The first arm 102 is at a proximal end 106 of the guide arm 100 and the second arm 104 extends from the first arm 102 to a distal end 108 of the guide arm 100. The second arm 104 extends along (or substantially along) a first axis x-x.

Still referring to FIG. 2, the second arm 104 terminates in a distal tip 110 at the distal end 108 of the guide arm 100. The distal tip 110 extends along (or substantially along) a second axis y-y. In an embodiment, the second axis y-y is approximately/substantially perpendicular to the first axis x-x. As shown in FIG. 2, an indicator feature 112 extends from the distal tip 110 to aid in proper alignment. In the depicted embodiment, the indicator feature 112 is a protrusion or other similar projection. As shown, the indicator feature 112 extends proximally from the distal tip 110 toward the first arm 102 along a third axis z-z. In the preferred embodiment, the third axis z-z is substantially parallel to the first axis x-x. Accordingly, the second axis y-y is substantially perpendicular to the third axis z-z.

Figure 3:
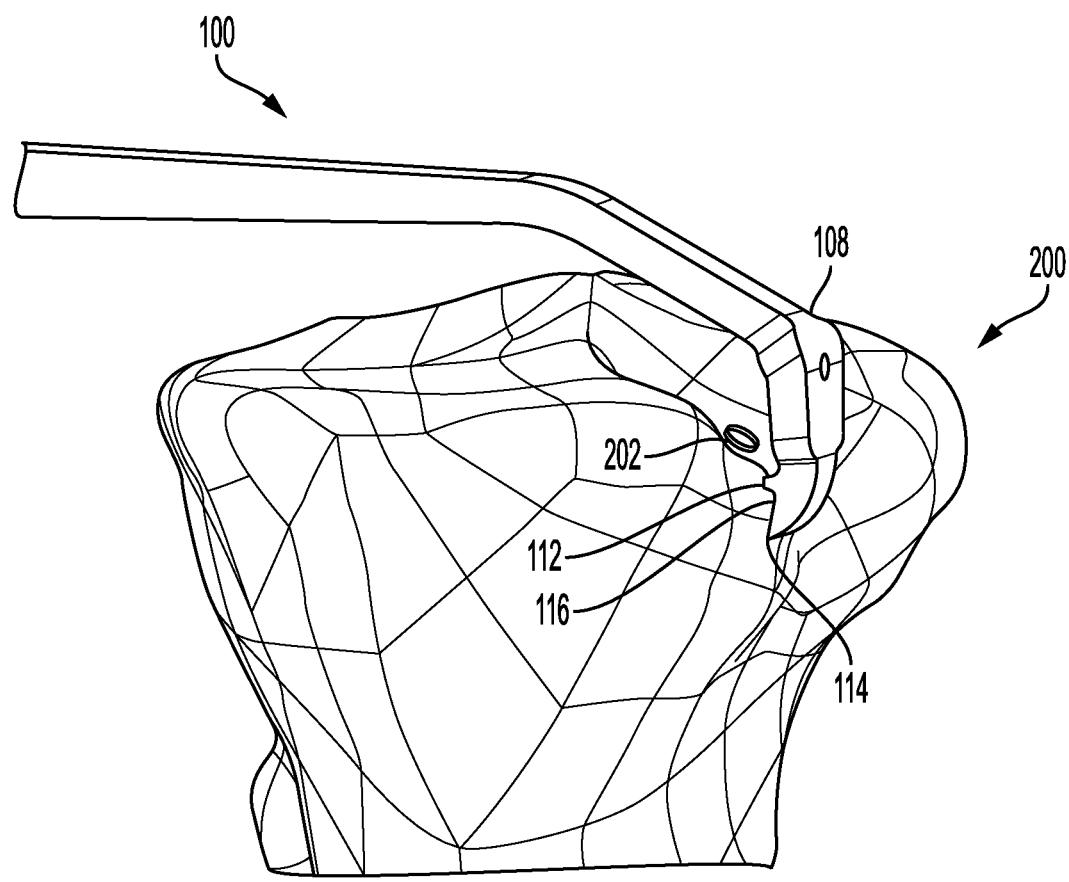
FIG. 3 is a side perspective view schematic representation of the drill guide arm on a bone, according to an embodiment.

Turning now to FIG. 3, there is shown a side perspective view schematic representation of the drill guide arm 100 on a bone 200, according to an embodiment. In the depicted embodiment, the distal end 108 of the guide arm 100 is positioned around the knee bone 200. As shown in FIG. 3, the bone 200 comprises an exit point 202 where an accessory pin can exit the bone 200. The indicator feature 112 of the guide arm 100 provides a visual reference for the level of the accessory pin's exit point 202. In addition, the indicator feature 112 rests on the bone 200, specifically, the posterior ridge of the knee, as shown.

Figure 4:
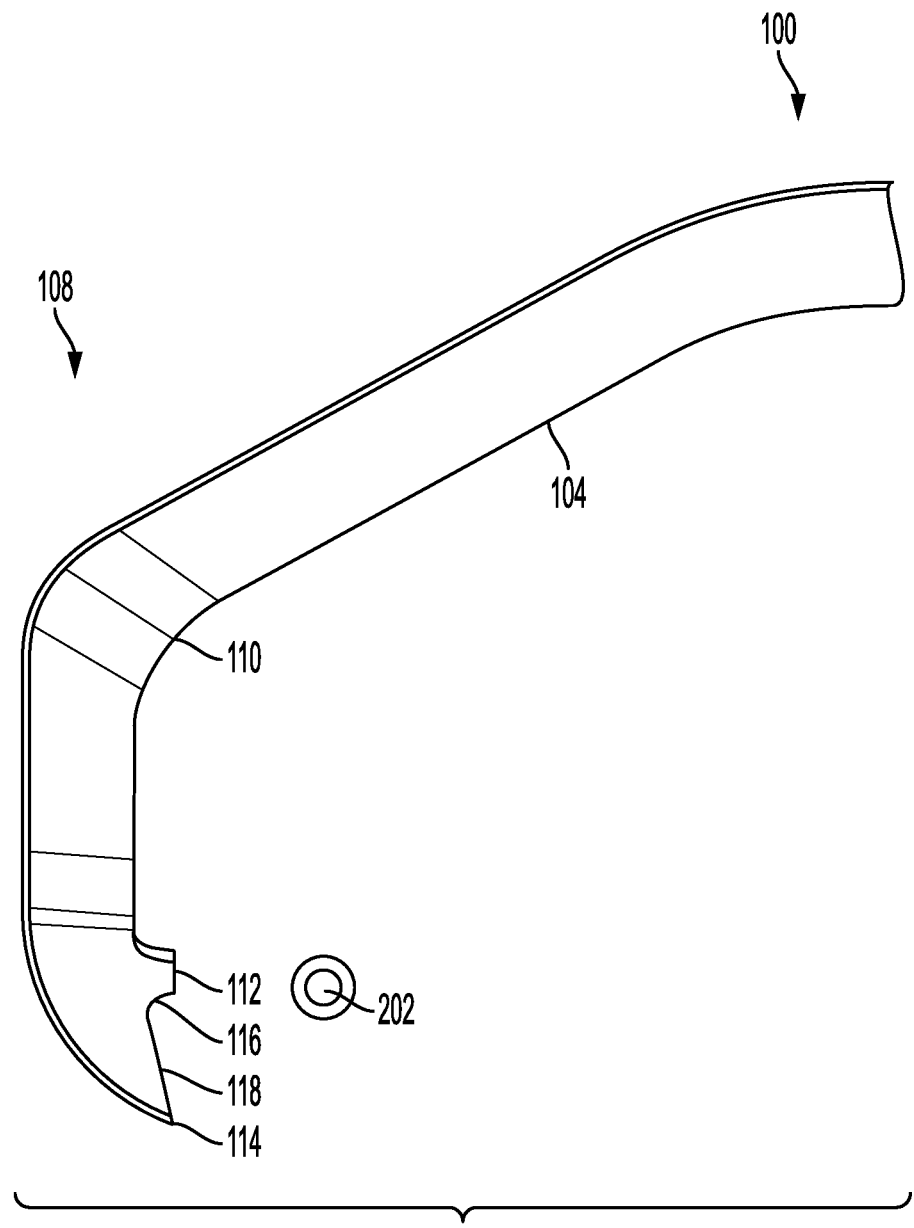
FIG. 4 is a close-up side view schematic representation of the distal end of the drill guide arm, according to an embodiment.

Referring now to FIG. 4, there is shown a close-up side view schematic representation of the distal end 108 of the drill guide arm 100, according to an embodiment. As can be seen in both FIGS. 3 and 4, the indicator feature 112 is off-set from the exit point 202. The off-set relationship prevents breaching of the wall of the bone tunnel by the distal end 108 of the guide arm 100. Although the indicator feature 112 is off-set from the exit point 202 in FIGS. 3-4, it is still substantially aligned with the exit point 202, indicating the level of the exit point 202.

As also shown in FIG. 4, the distal tip 110 is connected to the second arm 104 at an angle. The angle of the distal tip 110 relative to the second arm 104 provides retraction of soft tissue to provide direct visualization of a drill or drill pin as it exits the bone 200 (as should be understood by a person of ordinary skill in the art in conjunction with a review of this disclosure). To increase visualization, the guide arm 100 can be constructed from a radiopaque material to allow for visualization of the indicator feature 112 while drilling with imaging guidance.

In FIGS. 3-4, the distal tip 110 of the guide arm 100 can include a sharp point (or edge) 114. The sharp point 114 serves as an elevator to remove soft tissue from the bone 200. As also shown in FIGS. 3-4, the distal tip 110 includes a notch 116 formed by an undersurface 118 (FIG. 4) of the indicator feature 112 and the sharp point 114. In an embodiment, the notch 116 can be rough, comprising a plurality of small ridges or other protrusions (not shown). The notch 116 is used to capture the edge of the posterior ridge of the knee (bone 200), as shown in FIG. 3.

Figure 5:
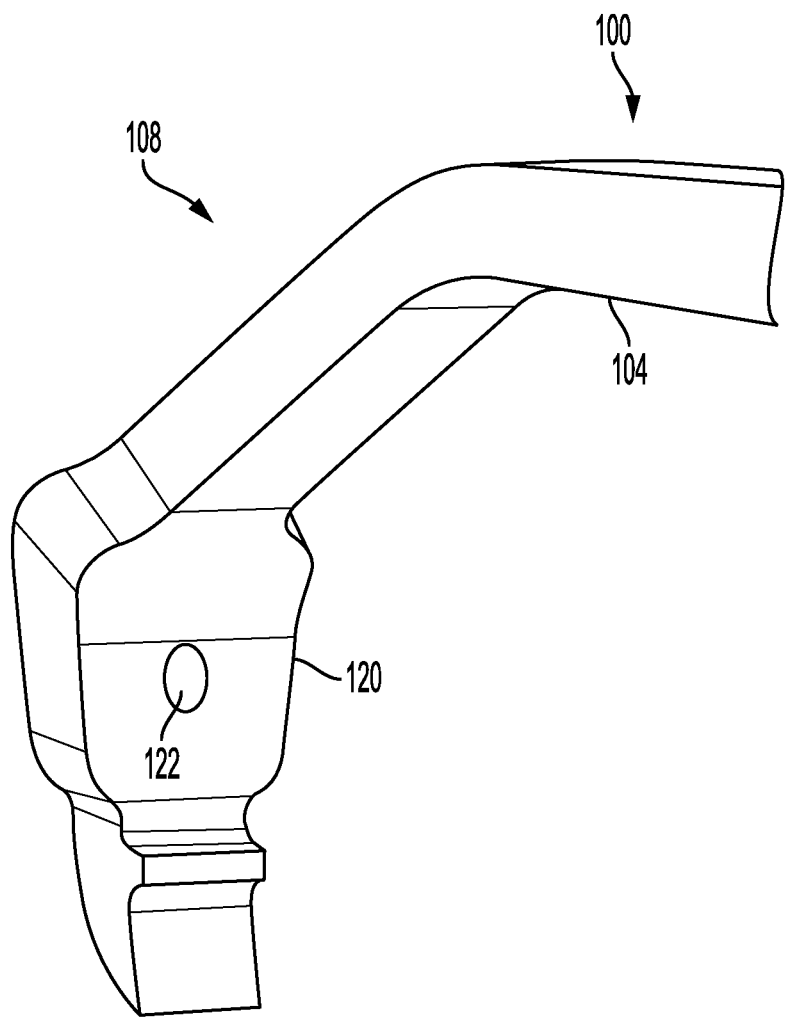
FIG. 5 is a close-up perspective view schematic representation of the distal end of the drill guide arm, according to an embodiment.

Turning now to FIG. 5, there is shown a close-up perspective view schematic representation of the distal end 108 of the drill guide arm 100, according to an embodiment. The distal tip 110 comprises a shield feature 120 configured to provide protection against the drill or drill pin. If the drill and/or drill pin extends past the distal tip 110 of the guide arm 100, each could damage critical neurovascular structures located on the posterior side of the knee. The shield feature 120 of the distal tip 110 comprises a width that is larger than a width of the remainder of the distal tip 110. In the depicted embodiment, the shield feature 120 can be tapered such that it allows for unobstructed insertion through the intercondylar notch space of the knee.

Still referring to FIG. 5, the shield feature 120 of the distal tip 110 includes an aperture 122 extending therethrough. The aperture 122 is configured to accept the tip of a guide pin (not shown). The guide pin can extend through the aperture 122 in the shield feature 120, which prevents excursion of the guide pin through the back of the knee while a cannulated drill is used over the guide pin. The aperture 122 can extend part of the way through or all of the way through the shield feature 120.

All definitions, as defined and used herein, should be understood to control over dictionary definitions, definitions in documents incorporated by reference, and/or ordinary meanings of the defined terms.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. A guide arm, comprising:
   a first arm at a proximal end connected at an angle to a second arm, the second arm extending to a distal end along a first axis;
   wherein the angle is within range of 80°-110°;
   a distal tip extending from the second arm at the distal end;
   a shield feature of the distal tip, the shield feature having a width wider than a portion of the distal end immediately proximal to the shield feature and a portion of the distal end immediately distal to the shield feature, and an aperture extending at least partially through the shield feature.

2. The device of claim 1, wherein the distal tip extends along a second axis.

3. The device of claim 2, wherein the second axis is substantially perpendicular to the first axis.

4. The device of claim 1, wherein the angle is within range of 90°-100°.

5. The device of claim 1, wherein the shield feature is tapered.

6. The device of claim 1, further comprising a sharp point on the distal tip.

7. The device of claim 6, wherein the sharp point is angled toward the proximal end.

8. The device of claim 1, wherein the guide arm is composed of radiopaque material.

9. The device of claim 1, wherein the distal tip extends at an angle relative to the second arm.

* * * * *